United States Patent [19]

Bonnefous et al.

[11] Patent Number: 5,320,105

[45] Date of Patent: Jun. 14, 1994

[54] ULTRASONIC ECHOGRAPH FOR MEASURING HIGH VELOCITIES OF BLOOD FLOWS

[75] Inventors: Odile Bonnefous, Nogent; Antoine Goujon, Paris, both of France

[73] Assignee: U.S. Philips Corporation, New York, N.Y.

[21] Appl. No.: 988,620

[22] Filed: Dec. 10, 1992

[30] Foreign Application Priority Data

Dec. 11, 1991 [FR] France ................... 91 15374

[51] Int. Cl.$^5$ .................................................. A61B 8/00
[52] U.S. Cl. ........................... 128/661.08; 128/661.09; 128/661.01; 73/861.25
[58] Field of Search .............. 128/661.01, 661.08, 128/661.09, 661.10; 73/861.25

[56] References Cited

U.S. PATENT DOCUMENTS

| | | | |
|---|---|---|---|
| 4,799,490 | 1/1989 | Namekawa | 73/861.25 |
| 4,803,990 | 2/1989 | Bonnefous et al. | 128/661.08 |
| 4,955,386 | 9/1990 | Nishiyama et al. | 128/661.09 |
| 5,062,430 | 11/1991 | Bonnefous | 128/661.09 |
| 5,156,153 | 10/1992 | Bonnefous | 73/861.25 |
| 5,163,434 | 11/1992 | Kamazawa | 128/661.09 |
| 5,201,313 | 4/1993 | Katakura | 128/661.09 |

OTHER PUBLICATIONS

"Doppler Ultrasound and Its Use In Clinical Measurement", by Peter Atkinson et al, Academic Press, 1982, pp. 114–128.

Primary Examiner—William E. Kamm
Assistant Examiner—George Manuel
Attorney, Agent, or Firm—Jack D. Slobod

[57] ABSTRACT

An echograph includes a transmission stage (20), a circuit (31) for suppressing fixed echos, and a correlation-interpolation circuit (33).

The the transmission stage (20) transmits a pulsed signal having two neighboring, alternating recurrent periods $T_1$ and $T_2$, the fixed echo suppression circuit (31) being adapted to double the recurrent period and comprises two outputs having the index even and odd, the correlation-interpolation circuit (33) performing, for each velocity, two distinct correlations, one of which is associated with the period $T_1$ whereas the other is associated with the period $T_2$, after which these two correlations are compared so as to derive a non-ambiguous velocity value therefrom.

6 Claims, 2 Drawing Sheets

ULTRASONIC ECHOGRAPH FOR MEASURING HIGH VELOCITIES OF BLOOD FLOWS

FIELD OF THE INVENTION

The present invention relates to an ultrasonic echograph for measuring velocity profiles of blood flows, comprising at least one ultrasonic transducer which is connected to a stage for the transmission of a recurrent pulsed signal and to a stage for receiving echographic signals returned to the transducer and for processing the signals received, and also comprising a digital processing channel which consists successively of a circuit for suppressing fixed echos, a memory for digital samples, a correlation-interpolation circuit, and a validation circuit.

The invention can be particularly advantageously used as a profilometer and as a bidimensional colour display device in the field of echographic examination of blood flows in vessels, notably the exact detection of stenosis of arteries.

The general technical problem to be solved by any device for the measurement of the velocity of moving organs and blood flows is to obtain an exact as possible estimate of the axial velocity of the movement being studied in order to form, using display devices, exact mages of the organs and the blood flows subjected to an ultrasonic echographic examination.

BACKGROUND OF THE INVENTION

For several years various solutions have been proposed to this technical problem. In this respect European Patent Application No. 0 225 667 which corresponds to commonly owned U.S. Pat. No. 4,803,990 describes a device of the kind set forth for measuring the velocity of moving organs and blood flows which utilizes the fact that the successive ultrasonic signals returned by a moving target are related, in the case of recurrent transmission with a recurrent period T, by the following equation:

$$S_{n+1}(t) = S_n(t - \tau) \quad (1)$$

This means that the signal $n+1$ is the replica of the preceding signal n, except for a time shift $\tau$. The latter represents the additional time required by the ultrasonic wave to travel the transducer-target-transducer path from one activation to another. In other words:

$$\tau = 2VT/C$$

where V is the velocity of the target and C is the velocity of sound. It appears that measurement of $\tau$ enables measurement of the desired velocity V.

The correlation function between $S_n(t)$ and $S_{n+1}(t)$, defined by:

$$C_{n,n+1}(to,u) = \int_{to}^{to+W} S_{n+1}(t + u) S_n(t) dt$$

verifies that:
$$C_{n,n+1}(to,u) + C_{nn}(to, u - \tau)$$

The time to is linked to the scanning depth z as to $= 2z/C$, and W is the integration window.

The function $C_{nn}(to,u)$ is an autocorrelation function and, therefore, it is maximum for $u = o$. Thus, a measurement of the time shift $\tau$, and hence of the velocity V, can be performed by searching the parameter u for which the function $C_{n,n+1}(to,u)$ is maximum. To this end, the correlation function is sampled, using a sampling step $\Delta t$, between $u_{min} = -I\Delta t$ and $u_{max} = I\Delta t$ in steps of 1 so as to obtain $2I+1$ correlation function values. The maximum value of these $2I+1$ values corresponding to $u = uo$ enables measurement of $\tau$ by utilizing the equality $\tau = uo$.

In order to eliminate the errors which are inherent of the sampling during the determination of the maximum of the correlation function, use can be made of a multiplexing-interpolation circuit which supplies, on the basis of the correlation function values, a more exact estimate of the velocity and the value of the corresponding correlation peak. French Patent Application FR-2 590 790 in the name of Applicant gives the subject matter of which is included in the aforementioned U.S. Pat. No. 4,803,990 an example of this type of processing of the echographic signal where the correlation between signals is a "1-bit" correlation in a sense that the signals $S_{n+1}$ and $S_n$ previously used are reduced to the sign of the ultrasonic signal. It is known that in that, case, the peak of the correlation function is shaped as an isosceles triangle. Knowledge of this shape enables complete reconstruction of the correlation peak by linear interpolation, starting from the highest point and its two neighbours, and hence exact determination of the position of uo.

This known method for the measurement of velocities, based on the analysis of the time shift, offers substantial advantages over other methods which are based, for example on frequency or phase shift. It notably allows for the use of troadband transmission signals, offering a high axial measurement resolution.

However, the method described above does not enable measurement of velocities exceeding a limit velocity $V_{lim}$ given by:

$$V_{lim} = \frac{C}{4} \frac{1}{f_o T} \quad (2)$$

where C represents the propagation velocity of the ultrasonic wave. This phenomenon, also known as "aliasing", is linked to the indetermination induced by the periodicity of the echographic signal. A detailed description is given in "Doppler Ultrasound and Its Use in Clinical Measurement", P. Atkinson and J. P. Woodcock, Academic Press, 1982, pp. 114-128.

For example, using a recurrent period T of 100 $\mu$s, a central acoustic frequency $f_o$ of 5 MHz, and a propagation velocity C of 1500 m/s, a limit velocity $V_{lim}$ of 75 cm/s occurs whereas, for example given blood flows can reach velocities which are substantially higher.

In order to increase the limit velocity of the measurement, it could be contemplated to decrease the frequency $f_o$, but this would reduce the accuracy of measurement and the resolution. Similarly, an increase of the recurrent frequency would lead to an undesirable reduction of the scanning depth.

Thus, the technical problem to be solved by the present invention is to realise a device for the measurement of the velocity of blood flows of the kind disclosed in the preamble, which device enables an increase of the limit velocity $V_{lim}$ of measurement without reducing the frequency $f_o$ and without increasing the recurrent frequency $1/T$.

Independent from the "aliasing" phenomenon, it is an object of the invention to remove other ambiguities which are linked to the sampling during the determination of the correlation peak. It may occur that the highest point of the sampled correlation function does not relate to the correlation peak searched. This situation may occur when complex streams are measured, comprising substantial speed gradients which tend to lower the correlation peak. This error becomes apparent as abrupt discontinuities in the reconstruction of the velocity profile as a function of the scanning depth.

A solution to the technical problem posed, known to Applicant, consists in that said device comprises a second processing channel for the echographic signal received, comprising two symmetrical bandpass filters $F_1$ and $F_2$ which act on the signal $S_n(t)$, are connected in parallel and supply the signals $s_{n1}(t)$ and $s_{n2}(t)$, respectively, which are centred around a frequency $f_1$ which is at the most equal to $f_o$ and around a frequency $f_2$ which is at least equal to $f_0$, respectively, the difference $f_2 - f_1$ being smaller than $f_0$, a multiplier which forms the product of the signals $S_{n1}(t)$ and $S_{n2}(t)$, a symmetrical low-pass filter which selects the component $S_n(t)$ of the frequency $f_2 - f_1$ of the product $S_{n1}(t) \times S_{n2}(t)$, a second correlation circuit which supplies $2I + 1$ sampled values of the correlation function of two successive signals $S_n(t)$ and $S_{n+1}(t)$, referred to as the second correlation function, a multiplexer-interpolation circuit producing an estimate of the velocity by searching the maximum of the first correlation function around the sample producing the greatest value of the second correlation function.

Thus, the known device utilizes not only a signal $S_n(t)$ of high frequency ($f_0$) like the prior art device, but also a second signal $S_n(t)$ of low frequency ($f_2 - f_1$) which also satisfies the relation (1) and which may thus be treated as the signal $S_n(t)$. The second correlation function, linked to the signal $S_n(t)$, has a frequency which is much lower and exhibits, in the measurement domain considered, substantially only one maximum, enabling total removal of the indetermination due to the "aliasing" phenomenon during the measurement of the velocity on the basis of the first correlation function. This device combines the advantages of a more exact measurement, determined by the signal of frequency $f_0$, and a higher limit velocity, imposed by the low-frequency signal, and having a value which is given by:

$$V_{lim} = \frac{c}{4} \frac{1}{(f_2 - f_1)T}$$

The known solution as disclosed in the foregoing paragraphs, however, does not allow for very high values to be obtained for the limit velocity. Actually, given the necessary separation of the filters $F_2$ and $F_1$ for selecting the frequencies $f_2$ and $f_1$, a ratio in the order of only from 2 to 3 can be obtained for the frequencies $f_0/f_2 - f_1$, enabling a gain from a value $V_{lim}$ of 0.8 m/s to a value in the order of 2 m/s. This is sufficient to measure all velocities of moving organs or flows in a healthy human body, but not for the measurement of given blood flows relating to pathological conditions, notably in the case of arterial stenosis, where the blood may reach velocities of 5 m/s, or arteriovenous shunts with blood velocities which are even higher.

Using the described known solution, when it is attempted to bring the frequencies of the filters $F_1$ and $F_2$ closer to one another, it is necessary to impart a much steeper cut-off edge thereto in order to prevent that they intersect one another, resulting in a parasitic DC component in their output signal. These filters then become more expensive because they are longer, which also implies the drawback of a loss of resolution and less exact correlations.

SUMMARY OF THE INVENTION

In accordance with the invention, the described technical problem is solved and the limitations of the prior art are overcome by an ultrasonic echograph as described above which is characterized in that said transmission stage comprises first means for transmitting said pulsed signal with two alternating, neighbouring, recurrent periods $T_1$ and $T_2$, said circuit for suppressing fixed echos comprising second suppression means which are adapted to the sum recurrent period of $T_1 + T_2$, as well as two outputs having the index even and odd, respectively, said correlation-interpolation circuit also comprising third means for performing, for each velocity, two distinct correlations, one of which is associated with the period $T_1$, whereas the other is associated with the period $T_2$, after which these correlations are compared so as to derive a non-ambiguous velocity value therefrom.

According to the prior art, the maximum depth that can be scanned is directly proportional to the recurrent period T. In accordance with the invention, this depth is limited by the shorter one of the two periods $T_1$ and $T_2$. Preferably, the values of $T_1$ and $T_2$ are chosen near the value customarily chosen for T, for example so that: $T_1 < T < T_2$. The suppression of fixed echos, indispensable in the case of a blood flow in order to eliminate the echos of very high amplitude from the walls of the vessel, implies a periodicity of the instants of transmission (activation) of the pulses. This periodicity, being equal to T according to the prior art, now becomes equal to the sum $T_1 + T_2$, regardless of the parity of the activation of a pulse considered. However, to each parity (even or odd) there corresponds a particular output signal at the output of the circuit for suppressing fixed echos and, downstream, two separate correlations correspond to these two signals. The comparison of the two correlation functions enables removal of any ambiguity which would be due to "aliasing" or sampling. It appears that in these circumstances the limit velocity that can be achieved by virtue of the above relation (2) is:

$$V_{lim} = \frac{c}{4} \frac{1}{f_0(T_2 - T_1)}$$

A compromise must be made for the choice of the values of $T_1$ and $T_2$. These values must be sufficiently distinct and separated from one another for a common peak of the two correlation functions to occur and, in the opposite sense, be near enough to one another so as to obtain a sufficiently high ratio $T/T_2 - T_1$ and hence also high limit velocity values. This compromise, however, is not critical and, for example the values of $T_1$, T and $T_2$ may be chosen so that:

$T_1 = 5 \, T_0, \ T = 5.5 \, T_0$ and $T_2 = 6 \, T_0$.

The invention will be described in detail hereinafter with reference to the accompanying drawings.

DESCRIPTION OF PREFERRED EMBODIMENTS

Figure 1:
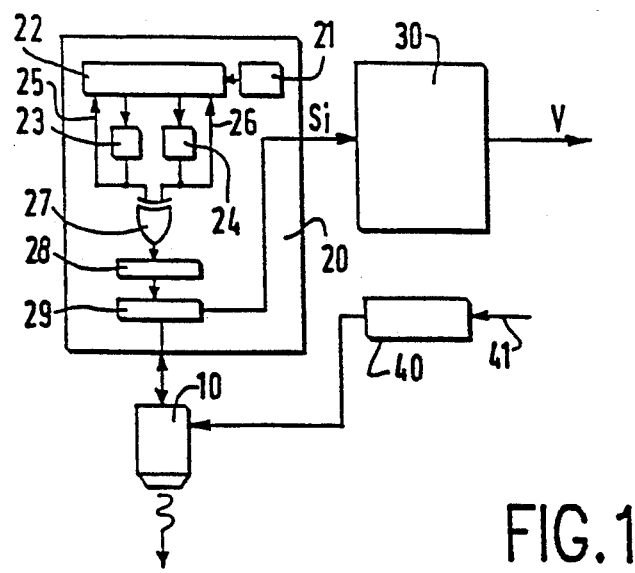
FIG. 1 shows the block diagram of an ultrasonic echograph in accordance with the invention.

The apparatus for scanning by means of ultrasonic echography as shown in FIG. 1 comprises, in a conventional manner, an ultrasonic transducer 10 which is connected on the one hand to a transmission stage 20 and on the other hand to a receiving and processing stage 30, as well as a mechanical scan control device 40 for the transducer. Instead of this single transducer there is preferably used an array of transducers which are then connected to an electronic scan control device. The transmission stage 20 comprises an electric excitation signal generator whose signals are applied to the transducer 10 which, in known manner, converts the signals into periodic trains of ultrasonic pulsed signals, transmission being controlled by clock signals supplied at a recurrent frequency $F=1/T$, for example in the order of 5 kHz, determined by an internal sequencer of the transducer 10. In accordance with the invention, the transmission stage 20 comprises first means for transmitting the trains of pulsed signals with two alternating, neighbouring recurrent periods $T_1$ and $T_2$. These first means, whose concept per se is known to those skilled in the art, are formed, for example by a clock generator 21 which applies a squarewave signal of the frequency $1/T_0$, for example $1/T_0=27.5$ kHz, to a logic circuit 22, the two outputs of which are connected to two counters 23 and 24, respectively. The counters 23 and 24 are coupled end-around and the first counter 23 counts to n and the second counter 24 counts to p (for example, $n=5$ and $p=6$). The output of the counter 23 is connected to a second input 25 of the logic circuit 22 and the output of the counter 24 is connected to a third input 26 of the circuit 22. A pulse received on the input 25 deactivates the counter 23 so as to activate the counter 24, and a pulse received on the input 26 has the reverse effect. On the other hand, each of the outputs of these counters are connected to an input of an exclusive-OR gate 27, the output of which is connected to the input of a generator 28 for generating electric excitation signals. The counters 23 and 24 are, for example of the type 74F 160A or 74F 168 manufactured by PHILIPS. The output signal of the generator 28 is applied, via a separator 29, to the transducer 10 which converts those signals into periodic trains of ultrasonic pulsed signals comprising from 4 to 10 pulses. The separator 29 between the transmission stage 20 and the receiving and processing stage 30, inserted between the transducer 10, the generator 28 and said stage 30 in a customary manner, prevents the overloading of the receiving circuits by the transmission signals. For the values chosen as described above: $T_0=36.4$ μs, $n=5$ and $p=6$, the values: $nT_0=182$ μs ($1/T_1=5.5$ kHz) and $pT_0=218$ μs ($1/T_2=4.58$ kHz) are obtained for the alternating recurrent periods of the pulses. These period values are to be compared with that currently adopted for T in the prior art: $T=200$ μs ($1/T=5$ kHz).

The device 40 is controlled by a clock signal which is applied to an input 41 and which has a frequency of, for example 1 kHz. In the most frequent case where the member 10 is a transducer array, the device 40 serves to produce, upon transmission, a distribution rule for distribution from one elementary transducer to another so as to focus the ultrasonic wave in the depth direction in conformity with a straight line which is substantially perpendicular to the medium (the body) scanned.

The receiving and processing stage 30 in known manner comprises, connected to the output of the separator 29, and RF amplifier (not shown) with gain compensation as a function of the depth, followed by a processing channel which comprises a cascade connection of a fixed echo suppression circuit, a digital sample memory, a correlation-interpolation circuit, and a validation circuit. In accordance with the invention, this processing channel (shown in FIG. 2) has given specific aspects. The fixed echo suppression circuit 31, always required because of the very high amplitude of the echos from the blood vessel walls, should include second means adapted to double the recurrent period $T_1$ and $T_2$ as will be described hereinafter with reference to the FIGS. 5 and 6.

The output of the circuit 31 is not a single output as in the prior art, but a double output and for input samples $S_i$, the output samples wherefrom fixed echos have been removed are not samples $D_i$ but even output samples, for example on one output, so $D_{2k}$ (for $i=2k$), and odd output samples on the other output, so $D_{2k+1}$ (for $i=2k+1$). Thus, on one output samples appear which relate to the period $T_1$ and on the other output samples appear which relate to the period $T_2$. The memory 32 for storing samples (FIG. 2) is a double memory which, for a given pulse train, stores in a first half the samples $D_i$ of the even excitations which are associated, for example with the recurrent period $T_1$, and in a second half the samples $D_i$ of the odd excitations which are associated with the recurrent period $T_2$.

Figure 3:
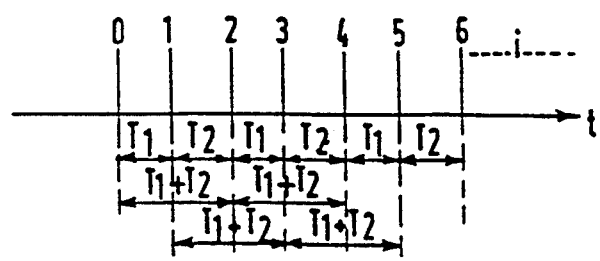
FIG. 3 shows a time diagram illustrating the clocking of the transmission of ultrasonic pulses in accordance with the invention.

The time diagram of FIG. 3 diagrammatically illustrates the transmission of a pulse train. Along the time axis there is plotted the instant which marks the start of each pulse, said instant being denoted by the rank number of the pulse within the train: 0, 1, 2, ..., i, ... or, on the basis of the parity: 0, 1, 2, ..., 2k, 2k+1, .... For example, as is shown, the pulses of even rank mark the start of a period $T_1$ between two successive pulses, and those of odd rank mark the start of a period $T_2$. According to the prior art, each train comprises approximately $N=10$ pulses (10 activations) which serve to form a mean value over N-n values for each velocity point, n being the number of coefficients of the filter for eliminating fixed echos. In conformity with the invention, given that said mean value is formed twice over $N/2-n$ values as will appear from the following description, it is advantageous to increase the number N to, for example 15. However, the value of N may not be increased too much, because otherwise the image rate is decreased for the case where the measured velocity profile is displayed on a monitor.

Figure 2:
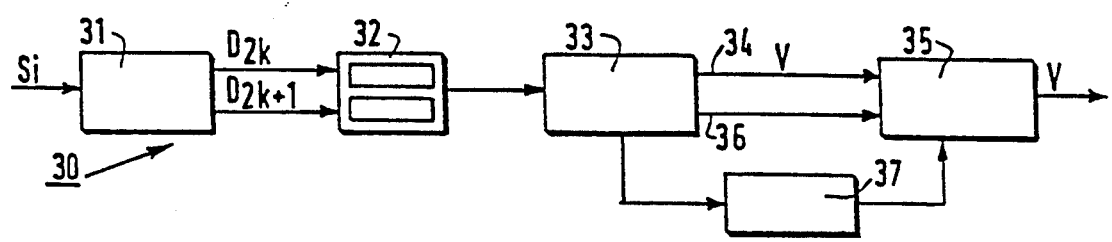
FIG. 2 shows the block diagram of the receiving and processing stage of FIG. 1.

The correlation-interpolation circuit 33 operates on the basis of 1-bit correlation as described in detail in the cited French Patent Application 2 590 790. In accordance with the invention, the circuit 33 comprises two 1-bit correlator assemblies. The known correlation circuit comprises, in a conventional manner, a delay line with a delay of one recurrent period T, enabling reception of two consecutive signals $D_i(t)$ and $D_{i+1}(t)$ at the same time. A correlator assembly in the circuit 33 processes, using a delay line with a delay of one recurrent period $T_1$, two consecutive even (or odd) signals $D_{2k}(t)$ and $D_{2k+2}(t)$ and the other correlator assembly processes, using a delay line with a delay of one recurrent period $T_2$, two consecutive odd (or even) signals $D_{2k+1}(t)$ and $D_{2k+3}(t)$, i.e. one correlator processes, for a first correlation function, two successive rows of the first half of the memory 32, each row corresponding to one activation, whereas the other correlator processes, for a second correlation function, two successive rows of the second half. In order to apply sample signals to the circuit 33, the addressing and reading of the memory 32 may be sequential, using a single data output, by reading a row of a given rank of the first half, followed by the reading of the same rank of the second half, as shown in FIG. 2, or even simultaneous on two outputs, each of which extracts one half of the memory. In each correlator, 2I+1 delay lines shift one of the two signals with respect to the other signal by an amount $u_j = j\Delta t$, j being an integer number taking the values $-I, -I+1, \ldots, -1, 0, 1, \ldots, I-1, I$, and $\Delta t$ being the sampling step, for example 50 ns. Finally, 2I+1 correlators supply 2I+1 sample values of each correlation function, thus defining a correlation window so that:

$C_{2K}^1$, $2K+2^{(t_o,u_j)}$ and $C_{2K+1}^2$, $2K+3^{(t_o,u_j)}$ j relating to [−I, I].

Figure 4A:
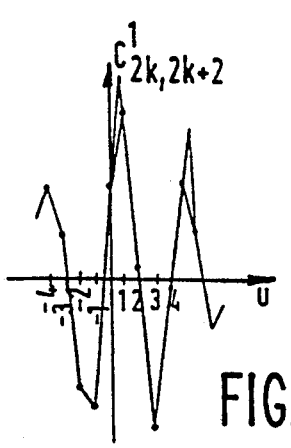
FIGS. 4a and 4b show at a and b, examples of correlation functions obtained by means of the echograph shown in FIG. 1.
Figure 4B:
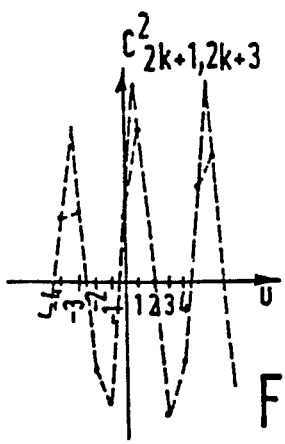

An example of such correlation functions is given in the FIGS. 4a and 4b, where I is greater than 4. On the basis of these two functions, a desired velocity point is obtained for the value of the abscissa $u_o = \tau$, which corresponds to the maximum correlation peak (principal peak), which value is theoretically the same for the two functions. In practice, each correlation function is stored and averaged, so as to achieve better immunity against noise, with the subsequent functions which correspond to the subsequent pairs of activations for the same depth $Z_o$ associated with $t_o$. However, for several reasons it may occur that the principal peak is not very distinct from secondary peaks: first of all, the correlation function is centered as regards frequency and oscillates in time with the mean frequency of the echographic signal. On the other hand, in the presence of noise, as is always the case, the signals are decorrelated and the correlation peak value may decrease to the same order as that of the secondary peaks created by the oscillation of the correlation function. Moreover, the sampling of the calculation of this function may also induce an ambiguity as regards the choice of the maximum sample before the interpolation, enabling the maximum of each correlation peak to be obtained.

In accordance with the invention, the search for the correlation peak is not restricted to a zone having the width of the period of the echographic signal (as expressed by the above relation (2)) and comparison of the correlation functions of the FIGS. 4a and 4b enables determination, with certainty, of the principal correlation peak from among several apparently possible peaks, as will be described hereinafter.

Figure 4C:
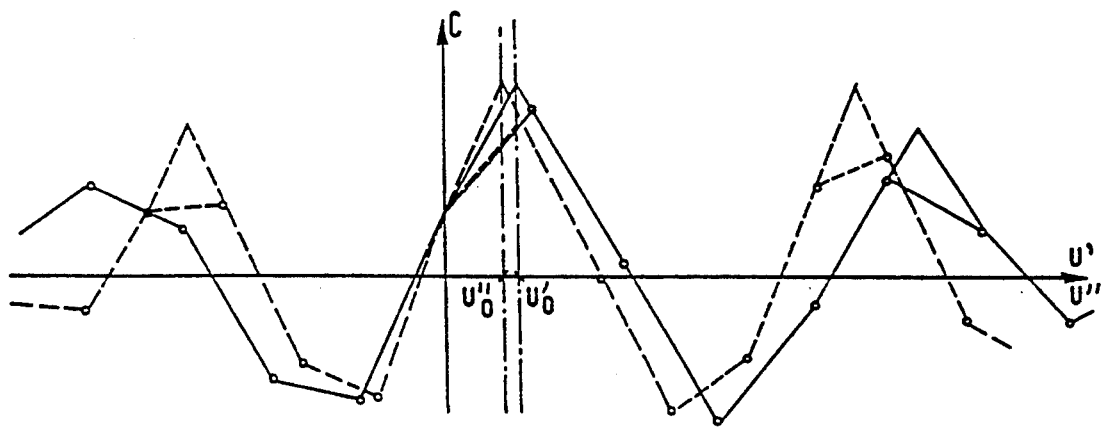
FIG. 4c shows how these functions are compared for the measurement of each velocity point searched.

The two correlation signals of the FIGS. 4a and 4b have the same period as the transmitted signal, but correspond to different pulse repetition frequencies (PRF). Consequently, the principal correlation peaks in each signal correspond to different time shifts (abscissa u), so: $\tau_1 = 2 \, V/C \, T_1$ and $\tau_2 = 2 \, V/C \, T_2$, V being the velocity value, searched. The scale of the time shifts between the two correlations is unified by extending them by a factor p for the first correlation (abscissa u') and n for the second correlation (abscissa u''), said correlations being superimposed as shown in FIG. 4c. Thus, each signal contains a correlation peak which has been shifted with respect to O by a period: $u'_o \sim u''_o \sim 2 \, V/C \, np \, T_o$ wherefrom the velocity V can be readily deduced. The selection of this peak is performed by retaining the peak which is common to the two correlations, the other peaks having been shifted by the expansion. Preferably, in order to ensure that only the significant peaks are considered, a thresholding to 50% of the maximum is imposed in advance on the correlation functions. In order to ensure that the peaks other than the principal peaks are all shifted two-by-two, it is necessary that the numbers n and p are mutual prime numbers. Actually, all possibilities of measurement of $\tau_1$ and $\tau_2$ are expressed by:

$\hat{\tau}_1 = \tau_1 + q/f_o$, so: $\hat{\tau}_1 = \tau_1$ modulo $1/f_o$ $\hat{\tau}_2 = \tau_2 + r/f_o$, so: $\hat{\tau}_2 = \tau_2$ modulo $1/f_o$ where $\hat{\tau}_1$ and $\hat{\tau}_2$ denote the estimated values of $\tau_1$ and $\tau_2$, respectively, and q, r are integer numbers.
Moreover:

$\tau_1 = \alpha n \, T_o$ $\tau_2 = \alpha p \, T_o$ where $\alpha = 2 \, V/C$;
by replacing $\tau_1$ and $\tau_2$ by their values in the preceding relations, the following equation is obtained:

$qp - rn = 0$.

In order to ensure that this equation has only one solution (except for the multiples of q and r), it is necessary that:

$q = n$ $r = p$ where n and p are mutual prime numbers.

The modulo to be applied to $\tau_1$ and $\tau_2$ is, therefore, $n/f_o$ and $p/f_o$, respectively.

Therefrom there is deduced (for example, on the basis of $\tau_2$):

$|\tau_2| \leq \frac{p}{2} \frac{1}{f_o}$ $2 \frac{V}{C} p T_o \leq \frac{p}{2} \frac{1}{f_o}$ -continued $$V \leq \frac{C}{4f_oT_o}$$

From comparison with the relation (2) it appears that the limit velocity which can thus be measured no longer relates to either $T_1$ or $T_2$ (as it does to T in the prior art), but relates to $T_0$, so a limit velocity multiplied by n (n being the smaller one of the two numbers n and p). The right-hand part of the diagram of FIG. 2 relates to a conventional situation and is described in French Patent Application 2 662 265 in the name of Applicant. After determination of each value of the mean velocity of the profile analysed, this value is applied, via a conductor 34, to a validation circuit 35 which is also referred to as a segmentation circuit and which receives directly from the circuit 33, via a conductor 36, the averaged value of the principal correlation peak and, via an amplitude calculation circuit 37, an estimate of the amplitude (energy) of the signal for the point of the profile considered. The velocity value is validated and supplied at the output of the circuit 35 only if the values of the two other parameters (correlation and amplitude) exceed predetermined thresholds.

The elimination of the fixed echos is customarily performed by forming successive differences or more complex combinations. In the case of a recurrent transmission with a period T, the successive reception signals are subjected to the following treatment:

$$D_1 = S_2 - S_1 \text{ (two coefficients 1 and } -1)$$

$S_1$ being delayed by T with respect to $S_2$ which is the signal received, or in a more refined manner:

$$D_1 = 2S_1 - S_2 - S_3 \text{ (three coefficients: 2, } -1 \text{ and } -1),$$

$S_1$ having been delayed by 2T and $S_2$ having been delayed by T with respect to $S_3$ which is the signal received.

In these two cases, each of the delay lines has a delay equal to the recurrent period of the transmission T. It is to be noted that for these two examples, if the relation:

$$S_i(t) = S_{i-1}(t-\tau) \text{ is true,}$$

the relation:

$$D_i(t) = D_{i-1}(t-\tau) \text{ is also verified.}$$

This means that the value of $\tau$ can be extracted by time correlation of the signals D in which the common (fixed) parts of the signals S have been eliminated. In accordance with the invention, this step for the suppression of fixed echos must be adapted because a double recurrence is used. In the signal transformation to be performed, it is necessary to preserve the recurrence relation of the delayed signals with respect to one another. It is to be noted that a periodicity, referred to as a general periodicity, exists in the transmission diagram of two alternating recurrences, which periodicity is equal to: $T_1 + T_2$ as indicated in FIG. 3, and also that the fact that overlapping occurs between one overall period and the next overall period complicates but not obstructs the elimination of the fixed echos.

The two recurrent relations linking the successive signals are:

$$S_{2k+1}(t) = S_{2k}(t - \tau_1)$$

$$S_{2k}(t) = S_{2k}(t - \tau_2)$$

Figure 5:
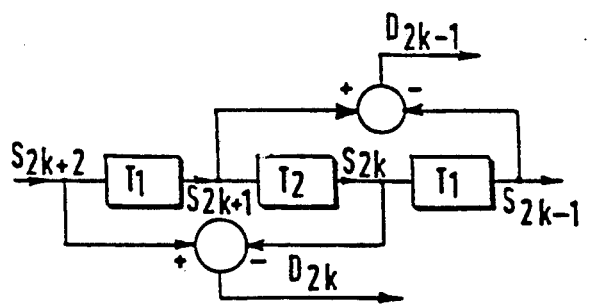
FIGS. 5 and 6 show the block diagrams of two embodiments of the circuit for suppressing fixed echos adapted to the invention.

As appears from FIG. 5, the new signals D wherefrom the fixed echos have been removed are generated as follows in the case of a single difference (two coefficients):

$$D_{2k}(t) = S_{2(k+1)}(t) - S_{2k}(t) = D_{2k-1}(t)$$

$$D_{2k-1}(t) = S_{2k+1}(t) - S_{2k-1}(t) = D_{2k-2}(t-\tau_1).$$

Figure 6:
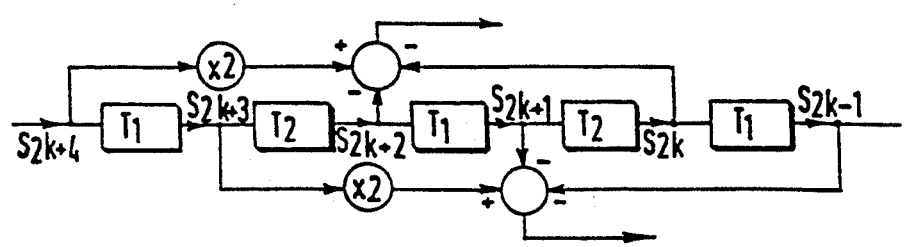

The case involving three coefficients, for example (2, $-1$, $-1$), is shown in FIG. 6:

$$D_{2k}(t) = 2S_{2(k+2)}(t) - S_{2(k+1)}(t) - S_{2k}(t) = D_{2k-1}(t - \tau_2)$$

$$D_{2k-1}(t) = 2S_{2k+3}(t) - S_{2k+1}(t) - S_{2k-1}(t) = D_{2k-2}(t-\tau_1).$$

We claim:

1. An ultrasonic echograph for measuring velocity profiles of blood flows, comprising at least one ultrasonic transducer which is coupled to a transmission stage for transmission of a recurrent pulsed signal and to a receiving and processing stage for receiving echographic signals returned to the at least one transducer and for processing the signals received, said receiving and processing stage comprising a digital processing channel which comprises, in cascade, a circuit for suppressing fixed echoes, a memory means for storing digital samples, a correlation-interpolation circuit, and a validation circuit, wherein said transmission stage comprises first circuit means for transmitting said pulsed signal with two alternating, neighboring recurrent periods $T_1$ and $T_2$, said circuit for suppressing fixed echoes comprises second circuit means for producing two outputs having even and odd indices, respectively, each output having a period equal to a sum $T_1 + T_2$ of the recurrent periods $T_1$ and $T_2$, said correlation-interpolation circuit comprises third means for performing, for each velocity, two distinct correlation to obtain respective correlation functions, one of which is associated with the period $T_1$ and the other of which is associated with the period $T_2$, for comparing these two correlation functions, and for deriving a non-ambiguous velocity value therefrom.

2. An ultrasonic echograph as claimed in claim 1, wherein the periods $T_1$ and $T_2$ are such that $T_1 = nT_0$, $T_2 = pT_0$, n and p being mutually indivisible numbers.

3. An ultrasonic echograph as claimed in claim 2, wherein $n = 5$ and $p = 6$.

4. An ultrasonic echograph as claimed in claim 1, characterized in that the comparing by said third circuit means comprises expanding the correlation functions associated with the periods $T_1$ and $T_2$ in abscissae by p and n, respectively, n and p being integer mutually indivisible numbers, superposing two expanded correlation functions thus obtained, and selecting, from amongst corresponding pairs of peaks of the correlation functions, a corresponding pair whose two abscissae are nearest one another.

5. An ultrasonic echograph as claimed in claim 3, wherein the periods $T_1$ and $T_2$ are such that $T_1 = nT_0$, $T_2 = pT_0$.

6. An ultrasonic echograph as claimed in claim 5, wherein $n = 5$ and $p = 6$.

* * * * *